US00PP24757P2

(12) United States Plant Patent
Verschoor

(10) Patent No.: US PP24,757 P2
(45) Date of Patent: Aug. 12, 2014

(54) ***VERONICA* PLANT NAMED 'PURPLE EXPLOSION'**

(50) Latin Name: ***Veronica* hybrid**
Varietal Denomination: Purple Explosion

(71) Applicant: Jan Verschoor, Haarlem (NL)

(72) Inventor: Jan Verschoor, Haarlem (NL)

(73) Assignee: A. Verschoor Horticulture Import-Export B.V., Haarlem (NL)

( * ) Notice: Subject to any disclaimer, the term of this patent is extended or adjusted under 35 U.S.C. 154(b) by 40 days.

(21) Appl. No.: 13/815,250

(22) Filed: Feb. 13, 2013

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Annette Para
(74) *Attorney, Agent, or Firm* — Penny J. Aguirre

(57) ABSTRACT

A new cultivar of *Veronica* plant, 'Purple Explosion', that is characterized by its flowers that are deep purple-pink in color, its compact inflorescences with numerous flowers, and its strong, tall stems making it desirable for cut flower use.

2 Drawing Sheets

Botanical classification: *Veronica* hybrid.
Variety denomination: 'Purple Explosion'.

CROSS REFERENCE TO A RELATED APPLICATION

This application is co-pending with a U.S. Plant Patent Application filed for a plant derived from the same breeding program that is entitled *Veronica* Plant Named 'Pink Bomb' (U.S. Plant patent application Ser. No. 13/815,251).

BACKGROUND OF THE INVENTION

The present invention relates to a new and distinct cultivar of *Veronica* plant of hybrid origin and will be referred to hereinafter by its cultivar name, 'Purple Explosion'. The new cultivar of *Veronica* is a hardy herbaceous perennial grown for landscape and cut flower use.

The new cultivar of *Veronica* was discovered as a naturally occurring whole plant mutation by the Inventor in a seed bed at his nursery in July of 2010 in Haarlem, The Netherlands. The exact parentage is unknown, however the seeds were collected, pooled, and sown from open pollinated plants of 'Pink Explosion' (U.S. Plant Pat. No. 22,592) and 'Blue Explosion' (U.S. Plant Pat. No. 22,497).

Asexual propagation of the new cultivar was first accomplished by stem cuttings by the Inventor in April of 2011 in Haarlem, The Netherlands. Asexual propagation by stem cuttings and division has shown that the characteristics of the new cultivar are stable and reproduce true to type in successive generations.

SUMMARY OF THE INVENTION

The following traits have been repeatedly observed and represent the characteristics of the new cultivar. These attributes in combination distinguish 'Purple Explosion' as a new and unique cultivar of *Veronica*.

1. 'Purple Explosion' exhibits flowers that are deep purple-pink in color.

2. 'Purple Explosion' exhibits compact inflorescences with numerous flowers.
3. 'Purple Explosion' exhibits strong, tall (70 to 75 cm in length) stems making it desirable for cut flower use.
4. 'Purple Explosion' can be most closely compared to its possible parent plants, 'Pink Explosion' and 'Blue Explosion'. 'Pink Explosion' differs from 'Purple Explosion' in having pink flowers and in having shorter stems (45 to 50 cm in length). 'Blue Explosion' differs from 'Purple Explosion' in having blue flowers and in having shorter stems (60 to 65 cm in length). 'Purple Explosion' can also be compared to 'Pink Bomb'. 'Pink Bomb' differs from 'Purple Explosion' in having pink flowers and in having shorter stems (55 to 60 cm in length).

BRIEF DESCRIPTION OF THE DRAWINGS

The accompanying colored photographs illustrate the overall appearance and distinct characteristics of the new *Veronica*. The photographs were taken of a plant about two years in age as grown outdoors in a field in Haarlem, The Netherlands and placed in a pot for the photographs.

The photograph in FIG. 1 provides a side view of 'Purple Explosion' in bloom.

Figure 1:
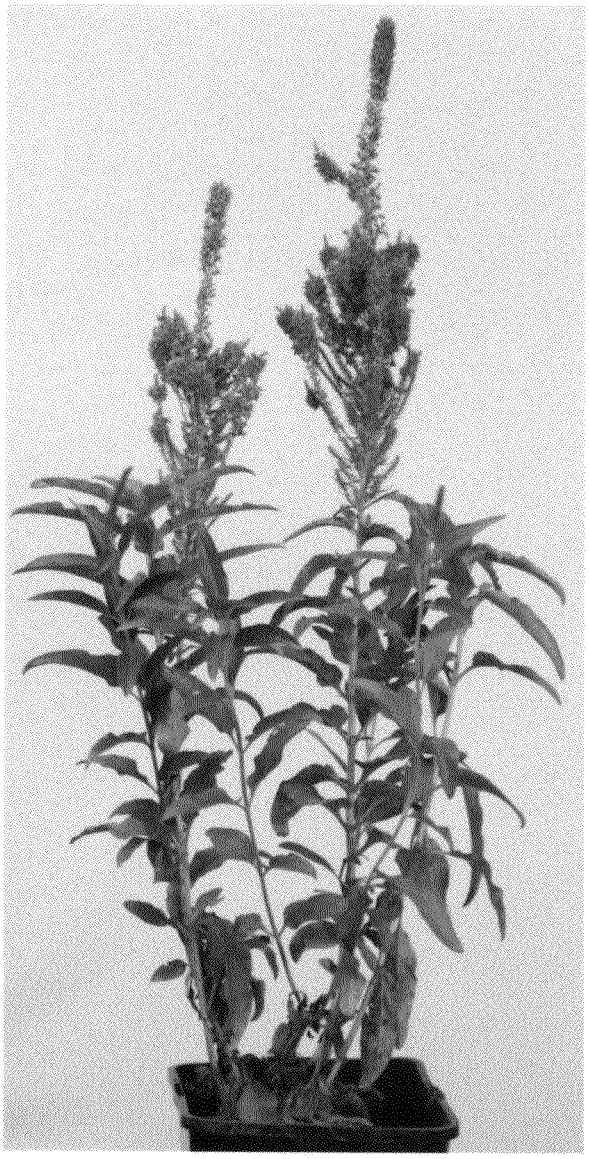
Figure 2:
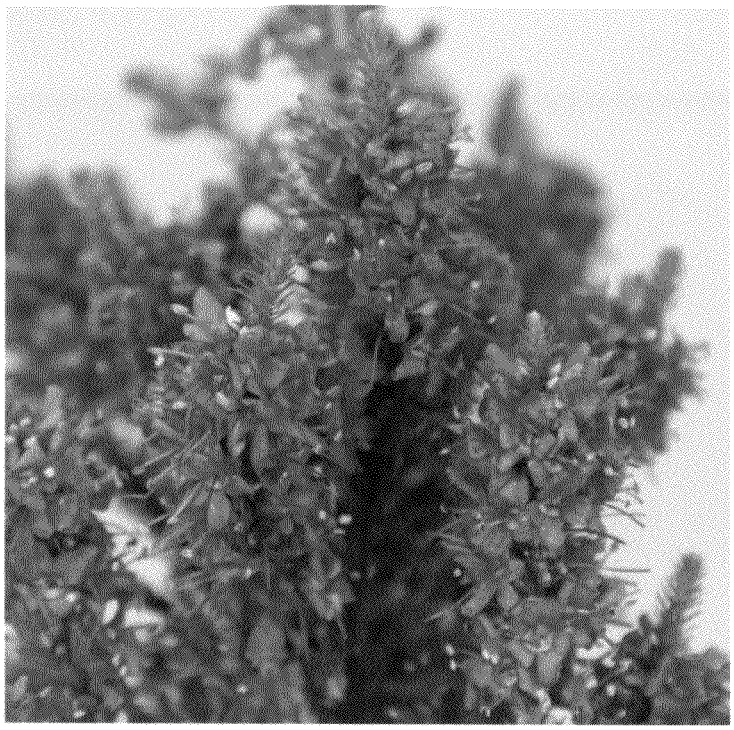

The photograph in FIG. 2 provides a close up view of the inflorescences of 'Purple Explosion'.

Figure 3:
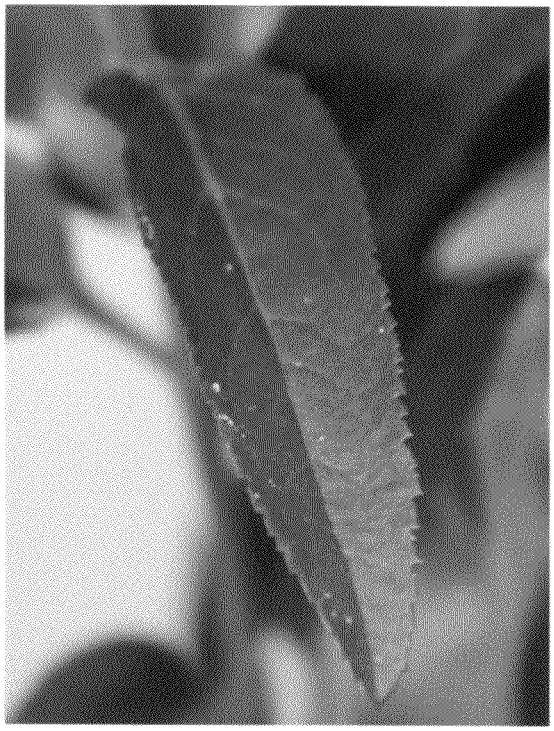

The photograph in FIG. 3 provides a close up view of a leaf of 'Purple Explosion'.

The colors in the photograph may differ slightly from the color values cited in the detailed botanical description, which accurately describe the colors of the new *Veronica*.

DETAILED BOTANICAL DESCRIPTION

The following is a detailed description of the new cultivar as observed for a plant about 2-years-old as field grown outdoors in Haarlem, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—About 8 weeks from mid summer to early autumn in The Netherlands.

*Plant type*.—Herbaceous Perennial.

*Plant habit*.—Upright with strong stems.

*Height and spread*.—Reaches about 75 cm in height and about 39 cm in spread.

*Hardiness*.—At least hardy in U.S.D.A. Zone 4.

*Diseases*.—No particular susceptibility or resistance to diseases has been observed.

*Root description*.—Fibrous.

*Propagation*.—Division and stem cuttings.

*Growth rate*.—Moderate.

Stem description:

*Shape*.—Round.

*Stem color*.—Between 143C and 144A.

*Stem size*.—70 to 75 cm in length (including peduncles) and an average of 4 mm in diameter.

*Stem surface*.—Slightly glossy and densely covered with soft pubescent hairs an average length of 0.4 mm and 157D in color.

*Branching number*.—Average of 7.

*Branching habit*.—Branching from the base.

Foliage description:

*Leaf division*.—Simple.

*Leaf arrangement*.—Opposite.

*Leaf shape*.—Narrowly ovate to lanceolate.

*Leaf size*.—An average of 7.9 cm in length and 2.6 cm in width.

*Leaf number*.—Average of 22 per lateral branch.

*Leaf base*.—Truncate.

*Leaf apex*.—Acute.

*Leaf margin*.—Serrate, average of 6 teeth per cm.

*Leaf venation*.—Pinnate, upper side 144A, lower side 144A to 144B.

*Leaf surface*.—Upper surface moderately glossy, lower surface slightly glossy, both surfaces sparsely covered with very short hairs an average of 0.3 mm in length and 157D in color.

*Internode length*.—An average of 3.2 cm.

*Leaf color*.—Mature upper surface N137B, mature lower surface; 147B, young upper surface; 143A, young lower surface; between 143A and 146B.

*Leaf attachment*.—Sessile.

*Petioles*.—Flattened, average of 2 mm height and width, 144A in color, surface pubescent.

Flower description:

*Inflorescence type*.—Compound terminal raceme.

*Lastingness of inflorescence*.—About 2 months in the garden.

*Lastingness as a cut flower*.—About 2 weeks.

*Inflorescence size*.—31.8 cm in height and 8.5 cm in width.

*Flower type*.—Campanulate.

*Flower number*.—About 1,250 per inflorescence.

*Flower fragrance*.—None.

*Flower buds*.—Narrow ovate to oblong in shape, about 5 mm in length and 1.5 mm in diameter, color 77A.

*Flower size*.—About 7.5 mm in depth and 7 mm in diameter.

*Peduncles*.—About 31.3 cm in length and 2 mm in width, primary racemes straight upright, secondary racemes in an average angle of 40°, strong in strength, 137C in color, surface is slightly glossy and densely covered with soft pubescent hairs an average length of 0.4 mm and 157D in color.

*Pedicels*.—An average of 1.75 mm in length and 0.5 mm in width, held at an average angle of 65°, strong in strength, 137C in color, surface is slightly glossy and densely covered with soft pubescent hairs an average length of 0.4 mm and 157D in color.

*Calyx*.—Rotate in shape, average of 1.8 mm in length and 2 mm in diameter.

*Sepals*.—4, about 0.75 mm in width and 1.8 mm in length, young upper surface color; 143A, young lower surface color; 143B, mature upper surface color; 143A, mature lower surface color; 143B to 143C, both surfaces dull and smooth, narrow ovate in shape, acute apex, cuneate base with lower 5% fused, entire margin.

*Petals*.—4, oblanceolate in shape, broadly acute apex, campanulate, lower 45% fused, entire margin, color: upper surface when opening; between 77A and N81B, lower surface when opening; N81B, upper and lower surface when fully open; N82A, fading to 86A to 86B, up to 6 mm in length and 2.5 mm in width, dull and smooth on upper and lower surface.

Reproductive organs:

*Gynoecium*.—1 Pistil, 7 mm in length, style is about 6.5 mm in length and N78B in color, stigma is clavate in shape and N78A in color, ovary is 144B in color.

*Androecium*.—2 stamens, filament is about 6 mm in length and N81B in color, anthers are dorsifixed and elliptic in shape, about 1.5 mm in length and N79C in color, pollen, is moderate in quantity and 11D in color.

*Fruit*.—Fruit and seed production was not observed under the conditions tested.

It is claimed:

1. A new and distinct variety of *Veronica* plant designated 'Purple Explosion' as described and illustrated herein.

* * * * *